US006589187B1

United States Patent
Dirnberger et al.

(10) Patent No.: US 6,589,187 B1
(45) Date of Patent: Jul. 8, 2003

(54) PRIORITIZED DYNAMIC MEMORY ALLOCATION OF ARRHYTHMIA EPISODE DETAIL COLLECTION

(75) Inventors: Denise Dirnberger, Blaine, MN (US); Ross O. Starkson, Minneapolis, MN (US)

(73) Assignee: Medtronic, Inc., Minneapolis, MN (US)

(*) Notice: Subject to any disclaimer, the term of this patent is extended or adjusted under 35 U.S.C. 154(b) by 238 days.

(21) Appl. No.: 09/733,301

(22) Filed: Dec. 8, 2000

(51) Int. Cl.[7] ............................. A61B 5/02; G06F 13/18; G11C 8/00
(52) U.S. Cl. ...................... 600/508; 600/513; 710/20; 710/244; 365/230.01; 711/151; 711/170
(58) Field of Search ................. 600/508, 509, 600/510, 515, 516, 517, 518, 519, 521, 523; 607/4, 5, 30, 32; 710/5, 20, 240, 244, 264, 268; 365/230.01, 230.08; 711/151, 170, 173

(56) References Cited

U.S. PATENT DOCUMENTS

| | | | |
|---|---|---|---|
| 4,814,974 A | * 3/1989 | Narayanan et al. | 710/244 |
| 4,920,489 A | 4/1990 | Hubelbank et al. | 600/519 |
| 5,002,062 A | 3/1991 | Suzuki | 600/509 |
| 5,052,399 A | 10/1991 | Olive et al. | 600/516 |
| 5,215,098 A | 6/1993 | Steinhaus et al. | 600/515 |
| 5,274,825 A | * 12/1993 | Lemay et al. | 710/268 |
| 5,313,953 A | 5/1994 | Yomtov et al. | 600/508 |
| 5,507,780 A | 4/1996 | Finch | 607/5 |
| 5,518,001 A | 5/1996 | Snell | 600/510 |
| 5,603,331 A | * 2/1997 | Heemels et al. | 600/508 |
| 5,732,708 A | 3/1998 | Nau et al. | 600/523 |
| 5,776,168 A | 7/1998 | Gunderson | 607/27 |
| 5,785,660 A | 7/1998 | Van Lake et al. | 600/523 |
| 5,908,392 A | 6/1999 | Wilson et al. | 600/509 |
| 5,935,081 A | * 8/1999 | Kadhiresan | 600/513 |
| 5,987,357 A | 11/1999 | Prutchi et al. | 607/36 |
| 6,208,579 B1 | * 3/2001 | Prutchi et al. | 365/230.01 |
| 6,253,260 B1 | * 6/2001 | Beardsley et al. | 710/20 |

* cited by examiner

Primary Examiner—Willis R. Wolfe
(74) Attorney, Agent, or Firm—Girma Wolde-Michael

(57) ABSTRACT

A software system implemented in a medical device includes an allocation scheme for allocating storage of cardiac data. The software system enables storing cardiac data in a plurality of addressable locations. When all available locations within the plurality of addressable locations are full, a scratch location is assigned based on predetermined episode type priorities and characteristics. The priorities represent a graduated order based on the clinical significance of the cardiac episode under consideration. The characteristics provide classifications based on fastest rate, longest duration and last to occur care for each of the priorities.

18 Claims, 7 Drawing Sheets

| | |
|---|---|
| 610A | LONGEST VT |
| 610B | FASTEST VT |
| 610C | LAST VT |
| 610D | LONGEST AT |
| 610E | FASTEST AT |
| 610F | LAST AT |
| 610G | LONGEST AF |
| 610H | FASTEST AF |
| 610I | LAST AF |
| 610J | LONGEST AFI |
| 610K | FASTEST AFI |
| 610L | LAST AFI |
| 610M | LONGEST 1=1 |
| 610N | FASTEST 1:1 |
| 610P | LAST 1:1 |
| 610Q | SCRATCH BUFFER |

FIG. 6

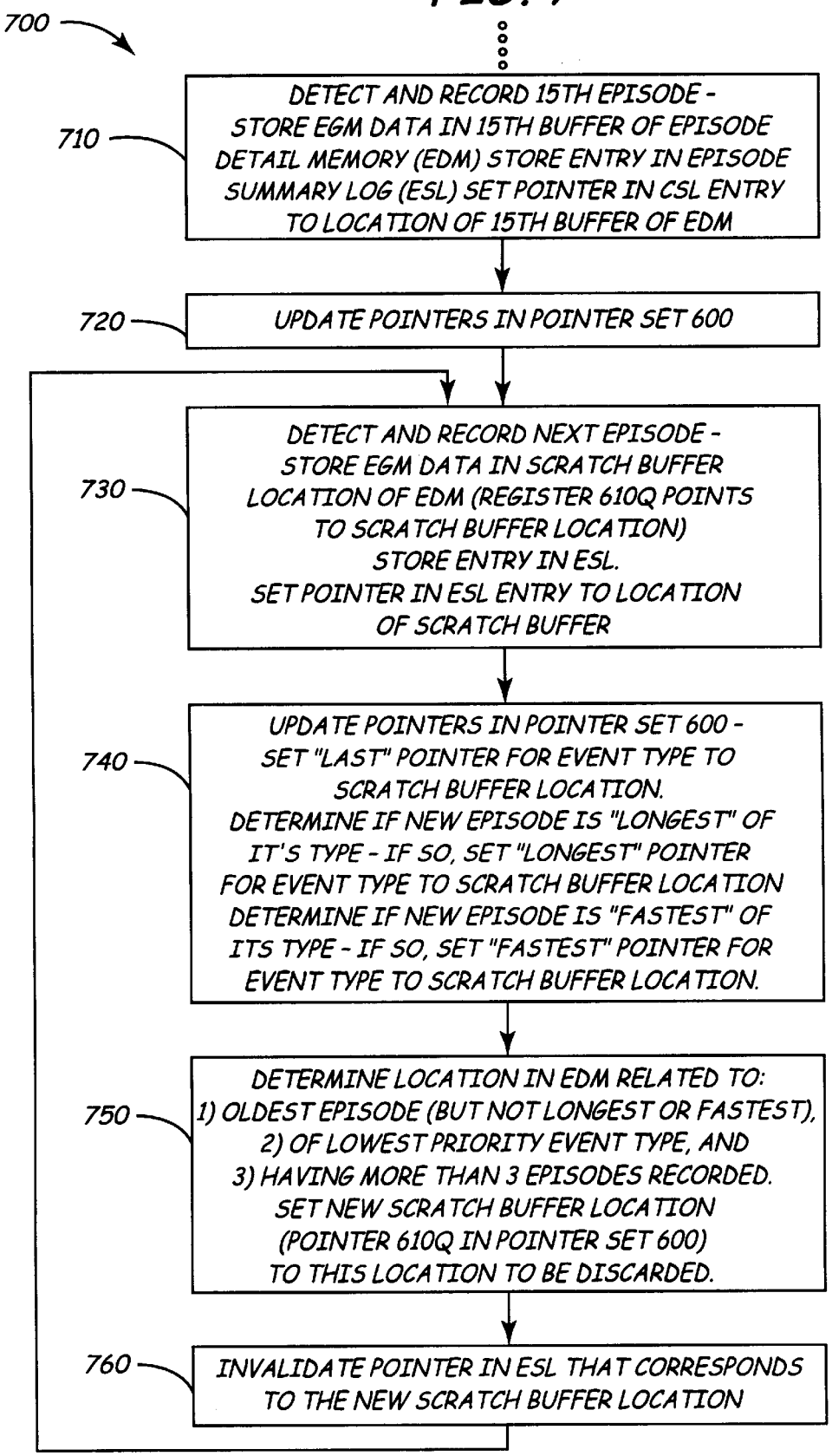

PRIORITIZED DYNAMIC MEMORY ALLOCATION OF ARRHYTHMIA EPISODE DETAIL COLLECTION

BACKGROUND OF THE INVENTION

1. Field of the Invention

The invention relates to the field of implantable medical devices, and, more particularly, to implantable devices that collect and store data associated with events occurring in the human body.

2. Description of the Related Art

Since the introduction of the first implantable pacemakers in the 1960s, there have been considerable advancements in both the field of electronics and of medicine, such that there is presently a wide assortment of commercially available body-implantable electronic medical devices. The class of implantable medical devices now includes pacemakers, implantable cardioverters, defibrillators, neurostimulators, and drug-administering devices, among others. Today's state-of-the-art implantable medical devices are vastly more sophisticated and complex than early ones, capable of performing significantly more complex tasks. The therapeutic benefits of such devices have been well-proven.

As the functional sophistication and complexity of implantable medical device systems have increased over the years, it has become increasingly advantageous for these devices to perform many functions beyond the rudimentary functions expected of them. For example, state-of-the-art cardiac pacemakers now perform many functions beyond simple monitoring and pacing. For example, these devices can now detect the onset of a variety of cardiac events, collect data associated with those events, and record that data for later retrieval and analysis. As one example, a modern cardiac pacemaker device can detect the onset of a ventricular tachycardia (VT) event, and it can record the date and time of the event, the duration of the event, and the heart rate observed during the VT event. This information may be stored within the implanted pacemaker and may be later retrieved by a clinician using a variety of well-known programmer devices. The clinician is thus able to gain valuable information regarding the patient's condition, enabling better-informed decisions regarding appropriate therapy.

Data associated with detected events may be stored in a "log" in random access memory (RAM) incorporated in the implanted device. Given the amount of memory available for the recording of such events, and in view of the amount of memory required to store the desired data for a single episode, a limited number of episodes may be recorded in the implanted device. For example, in a Model Kappa 700 pacemaker manufactured by Medtronic, data for a maximum of 17 episodes of each of three types may be stored in the pacemaker. That is, the log memory stores a maximum of 51 entries. Typically, several different types of events may be of interest. Using the limited amount of space available for recording information regarding these different event types, the allotted memory is typically divided into sections, with data regarding an episode being stored in the memory section allocated to that particular event type. Usually, the last occurring episode of an event type, the longest-lasting episode of an event type, and the episode having the fastest heart rate observed of an event type and several of the most recently occurring events will be stored into the log. After all episodes of a particular event type for which memory exists have been observed and recorded, all subsequent episodes of that type may simply be rejected. Meanwhile, if no episodes of a particular event type occur, the memory space allocated to that event type will remain unused.

Because of the above-described limitations, a doctor or clinician who seeks to maximize the amount of information available to him or her must decide which of the particular types of events he or she is most interested in observing. For example, by selecting only three types of events for data collection, the log memory may be allocated so as to provide for storage of up to five episodes of any particular event type. However, even under this scenario, valuable memory space will be wasted if no (or fewer than five, in this case) episodes of a selected event type occur. Moreover, the level of detail that is stored concerning any given episode is less than desirable.

The present invention overcomes, or at least reduces the effects of, some or all of the shortcomings associated with the above-described arrangements.

SUMMARY OF THE INVENTION

In one aspect of the present invention, an episode summary log memory is adapted to store a plurality of entries, each entry correlating to a cardiac event episode. An episode detail memory is adapted to store a plurality of sets of data associated with a particular cardiac event episode. At least one of the entries of the episode summary log memory includes a pointer to a corresponding at least one of the sets of data in the episode detail memory. In various embodiments of the present invention, both the episode summary log memory and the episode detail memory are allocated from random access memory (RAM), and each entry in the episode summary log memory may include a pointer to a corresponding set of data in the episode detail memory. The entries in the episode summary log may contain summary information regarding the cardiac event episode, whereas each of the sets of data in the episode detail memory includes detail information about the corresponding cardiac event episode.

In another aspect of the present invention, a method is provided for storing data associated with a cardiac event. The method includes detecting the cardiac event of interest, and recording data associated with that cardiac event. The data includes a date and time of the cardiac event, a duration of the cardiac event, a heart rate observed during the cardiac event, and EGM (electrogram referring to electrical signals from within the heart itself) data associated with the cardiac event. In specific implementations of the inventive method, the date and time, duration and heart rate may be recorded in a first memory while the EGM data is stored in a second memory. Moreover, in various implementations of the inventive method, a pointer may be set in the first memory to correlate an entry in the first memory with an entry in the second memory. In certain implementations of the method, a second cardiac event may be detected and recorded, a pointer may be set in the first memory in association with the second cardiac event, and a pointer associated with an earlier cardiac event in the first memory may be invalidated based on assigned cardiac event priorities and selected cardiac event characteristics.

BRIEF DESCRIPTION OF THE DRAWINGS

The invention may be understood by reference to the following description taken in conjunction with the accompanying drawings, in which like reference numerals identify like elements, and in which:

FIG. 6 illustrates one particular pointer set that may be used in an implementation of the present invention; and FIG. 7 illustrates a portion of one illustrative method according to the present invention.

Figure 1:
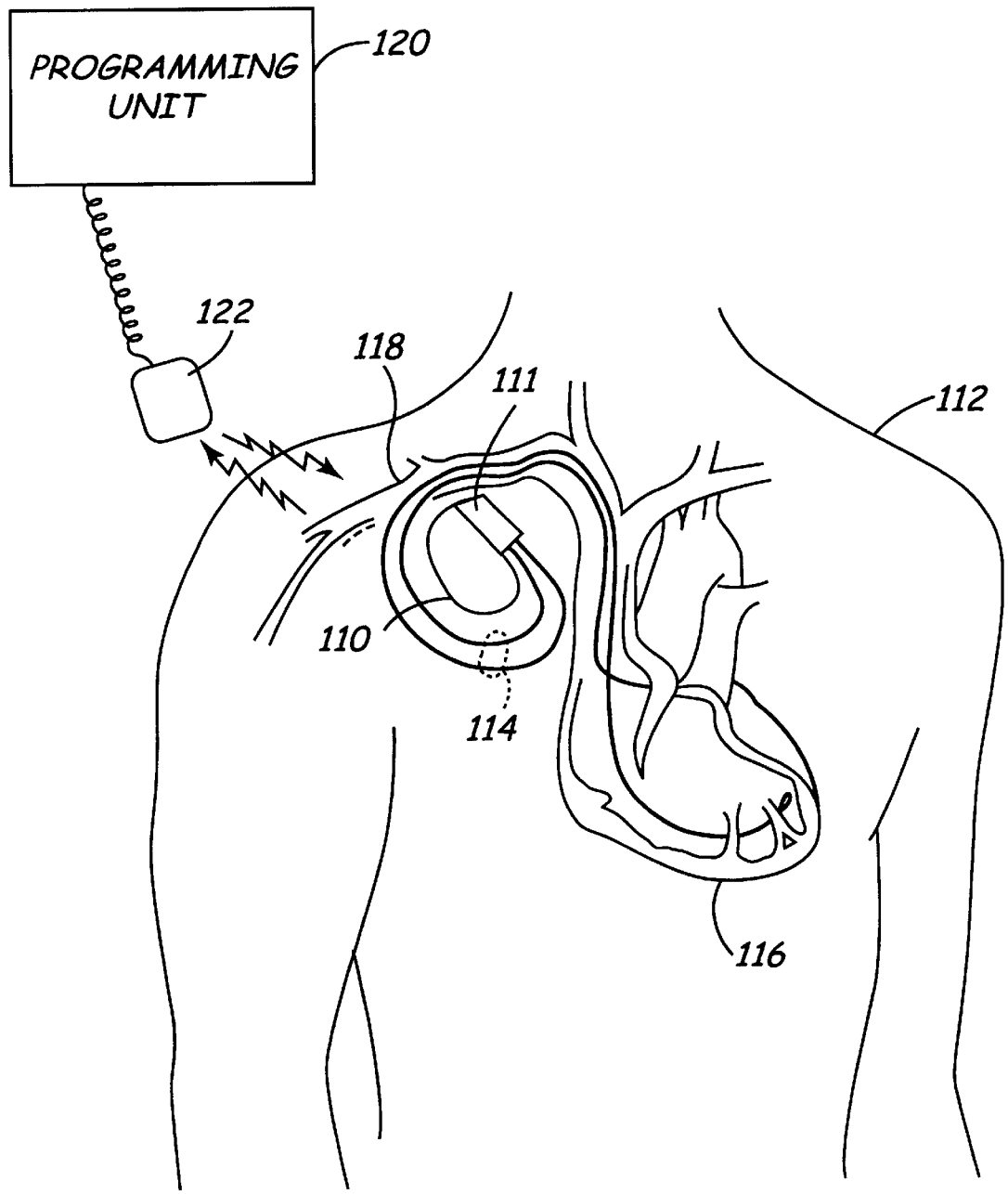
FIG. 1 illustrates a patient with an implantable pacemaker device implanted and a programmer device external to the patient.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF THE INVENTION

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The present invention will now be described with reference to the attached figures. The attached figures do not illustrate every feature of an implantable device, as such detail is not necessary for a complete understanding of the present invention. Rather, the figures illustrate those aspects of an implantable device that will be discussed in describing the present invention of an apparatus and a method. However, the inclusion of certain details within the figures and within the following description should not be regarded as necessary features of the claimed invention unless those features are specifically set forth in the appended claims.

FIG. 1 illustrates a patient 112 in which an implantable pacemaker 110 has been implanted. The pacemaker 110 is housed within a hermetically sealed, biologically inert outer canister or housing, which may itself be conductive so as to serve as an indifferent electrode in the pacemaker's pacing/sensing circuit. One or more pacemaker leads, collectively identified with reference numeral 114 in FIG. 1, are electrically coupled to the pacemaker 110 in a conventional manner and extend into the patient's heart 116 via a vein 118. Disposed generally near the distal end of leads 114 are one or more exposed conductive electrodes for receiving electrical cardiac signals or delivering electrical pacing stimuli to the heart 116. The leads 114 may be implanted with their distal end situated in either the atrium or ventricle of the heart 116.

FIG. 1 also depicts an external programming unit 120 for non-invasive communication with the implanted device 110 via uplink and downlink communication channels. Associated with the programming unit 120 is a programming head 122, in accordance with conventional medical device programming systems, for facilitating two-way communication between the pacemaker 110 and the programmer 120. In many known implantable device systems, a programming head such as that depicted in FIG. 1 is positioned on the patient's body over the implant site of the device (usually within 2–3 inches of skin contact), such that one or more antennae within the head can send RF signals to, and receive RF signals from, an antenna disposed within the hermetic enclosure of the implanted device or disposed within a connector block 111 of the device 110, in accordance with common practice in the art.

Using the programmer 120 and its programming head 122, various programming routines and/or data may be transmitted from the programmer 120 to the pacemaker 110 to add functionality to, or to alter existing functionality in, the pacemaker 110. In addition, data may be transmitted from the pacemaker 110 to the programmer 120. As will be discussed in greater detail below, the pacemaker 110 may, in addition to its functions of monitoring cardiac activity and generating therapy pulses as required, detect the onset of various arrhythmia conditions in the heart and collect information related to those conditions. For example, the pacemaker 110 may detect the onset of a ventricular tachycardia (VT) event, and in response to that detection, the pacemaker 110 may collect certain data associated with that VT episode. The date and time of the episode may be noted and recorded (as will be explained). The duration of the episode and the maximum heart rate observed during the episode may also be noted and recorded. Also, EGM data and marker data associated with the episode may be recorded. The pacemaker 110 includes certain programming routines designed to detect the onset of particular types of cardiac events, to determine the specific type of event, and to initiate the collection of certain data associated with the event. Those of ordinary skill in this art are familiar with such routines, and they will be fully able to prepare routines that are useful to a practice of the present invention upon a complete reading of this specification.

Figure 2:
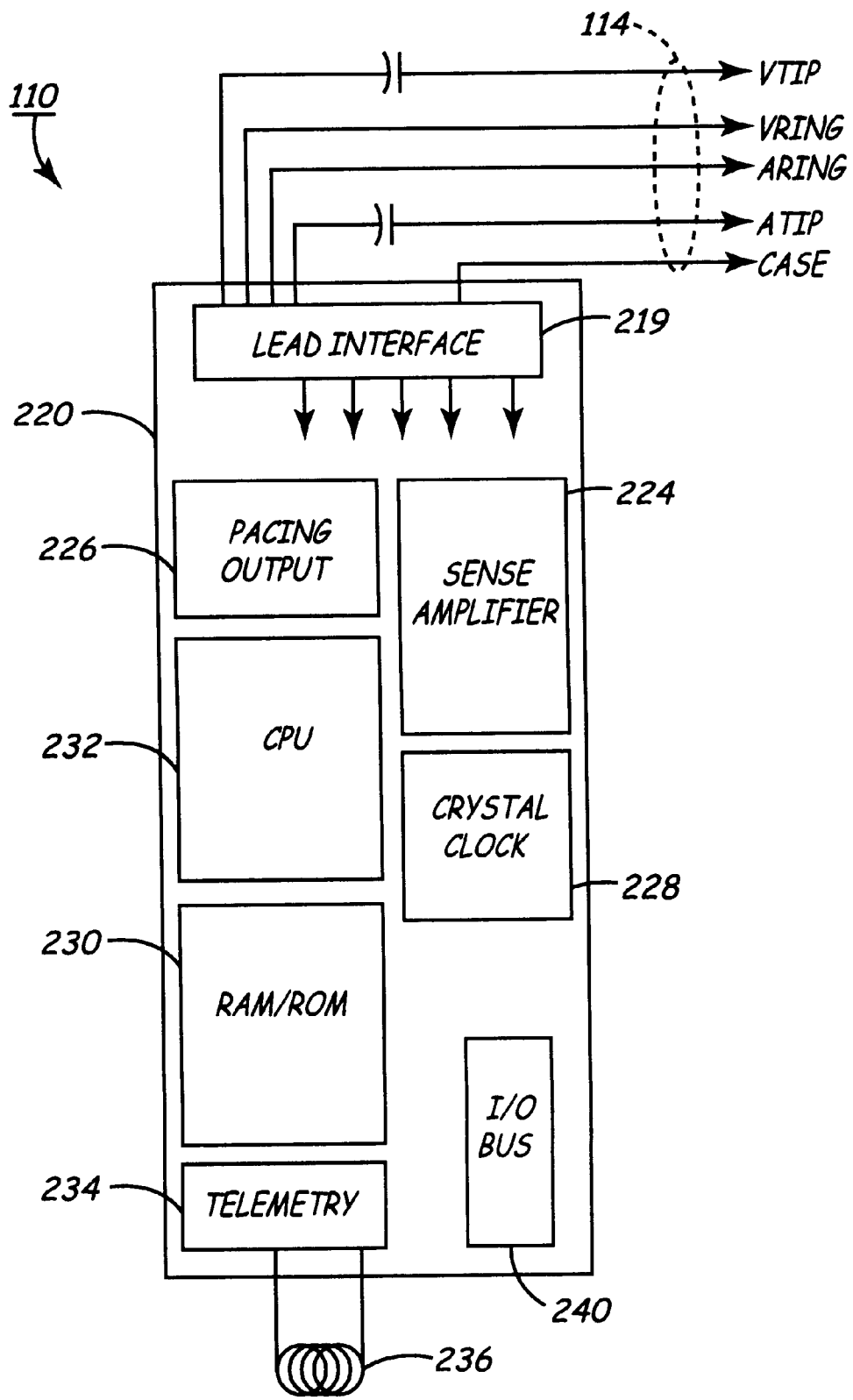
FIG. 2 is a block diagram of one illustrative pacemaker showing at least some of the main functional blocks in the pacemaker.

FIG. 2 provides a simplified block diagram of electronic circuitry that makes up the pacemaker 110 for delivery of electrical stimulation therapy to the patient. In FIG. 2, the pacemaker 110 comprises circuitry for controlling its pacing and sensing functions. The pacemaker circuitry may generally be of conventional design. To the extent that certain components of the circuitry of the pacemaker 110 are conventional in their design and operation, such components will not be described herein in detail, as it is believed that design and implementation of such components would be a matter of routine practice to those of ordinary skill in the art. For example, the circuitry of the pacemaker 110 shown in FIG. 2 includes sense amplifier circuitry 224, stimulating pulse output circuitry 226, a crystal clock 228, a random access memory and read only (RAM/ROM) unit 230, and a pacing timing and control circuit in the form of a programmed central processing unit (CPU) 232, all of which are well known in the art. The pacemaker 110 also includes an internal telemetry communication circuit 234 coupled to an antenna 236 so that it is capable of communicating with the external programmer/control unit 120. Various telemetry systems for providing the necessary uplink and downlink communication channels between an external programming unit and an implanted pacemaker are well known in the art.

With continued reference to FIG. 2, the pacemaker 110 is coupled to one or more leads 114 which, when implanted, extend transvenously between the implant site of the pacemaker 110 and the patient's heart 116, as previously noted with reference to FIG. 1. Physically, the connections between the leads 114 and the various internal components of the pacemaker 110 are facilitated by a conventional connector block assembly 11, shown in FIG. 1 but not shown in FIG. 2. Electrically, the coupling of the conductors of leads and internal electrical components in the pacemaker 110 may be facilitated by a lead interface circuit 219 which functions, in a multiplexer-like manner, to selectively and dynamically establish necessary connections between various conductors in the leads 114, including, for example, atrial tip and ring electrode conductors ATIP and ARING and ventricular tip and ring electrode conductors VTIP and VRING, and individual electrical components of the pacemaker 110, as would be familiar to those of ordinary skill in the art. For the sake of clarity, the specific connections between the leads 114 and the various components of the pacemaker 110 are not shown in FIG. 2, although it will be clear to those of ordinary skill in the art that, for example, the leads 114 will necessarily be coupled, either directly or indirectly, to sense amplifier circuitry 224 and stimulating pulse output circuit 226, in accordance with common practice, such that cardiac electrical signals may be conveyed to the sensing circuitry 224, and such that stimulating pulses may be delivered to cardiac tissue, via the leads 114. Also not shown in FIG. 2 is the protection circuitry commonly included in implanted devices to protect, for example, the sensing circuitry of the device from high voltage stimulating pulses.

As previously noted, the circuitry of the pacemaker 110 includes the central processing unit (CPU) 232 which may be an off-the-shelf programmable microprocessor or microcontroller, but in one embodiment of the invention is a custom integrated circuit. Although specific connections between the CPU 232 and other components of the pacemaker circuitry are not shown in FIG. 2, it will be apparent to those of ordinary skill in the art that the CPU 232 functions to control the timed operation of the stimulating pulse output circuit 226 and the sense amplifier circuit 224 under control of program instructions stored in the RAM/ROM unit 230. The crystal oscillator circuit 228 in the instant embodiment provides main clock timing. Again, the lines over which clocking signals are provided to the various timed components of the pacemaker 110 (e.g., microprocessor 232) are omitted from FIG. 2 for the sake of clarity. However, those of ordinary skill in the art will be familiar with such an operative arrangement.

It is to be understood that the various components of the pacemaker 110 depicted in FIG. 2 are powered by means of a battery (not shown), which is contained within the hermetic enclosure of the pacemaker 110, in accordance with common practice in the art. For the sake of clarity in the drawings, the battery and the connections between it and the other components of the pacemaker 110 are not shown.

The stimulating pulse output circuit 226 functions to generate cardiac stimuli under control of signals issued by the CPU 232. The sense amplifier circuit 224 functions to receive electrical cardiac signals from the leads 114 and to process such signals to derive event signals reflecting the occurrence of specific cardiac electrical events, including atrial contractions (P-waves) and ventricular contractions (R-waves). These event-indicating signals are provided to the CPU 232 for use by the CPU 232 in controlling the synchronous stimulating operations of the pulse generator 110 in accordance with common practice in the art. In addition, these event-indicating signals may be communicated, via uplink transmission, to the external programming unit 120 for visual display to a physician or clinician. Those of ordinary skill in the art will appreciate the pacemaker 110 may include numerous other components and subsystems, for example, activity sensors and associated circuitry. The presence or absence of such additional components in the pacemaker 110, however, is not believed to be pertinent to the present invention, which relates primarily to the recording of data associated with certain cardiac event episodes for later retrieval and analysis. Those of ordinary skill in the art will be able to select appropriate pacing output circuits, sense amplifier circuits and other components and subsystems that will be suitable for use in a pacemaker that also implements and practices the present invention.

Figure 3:
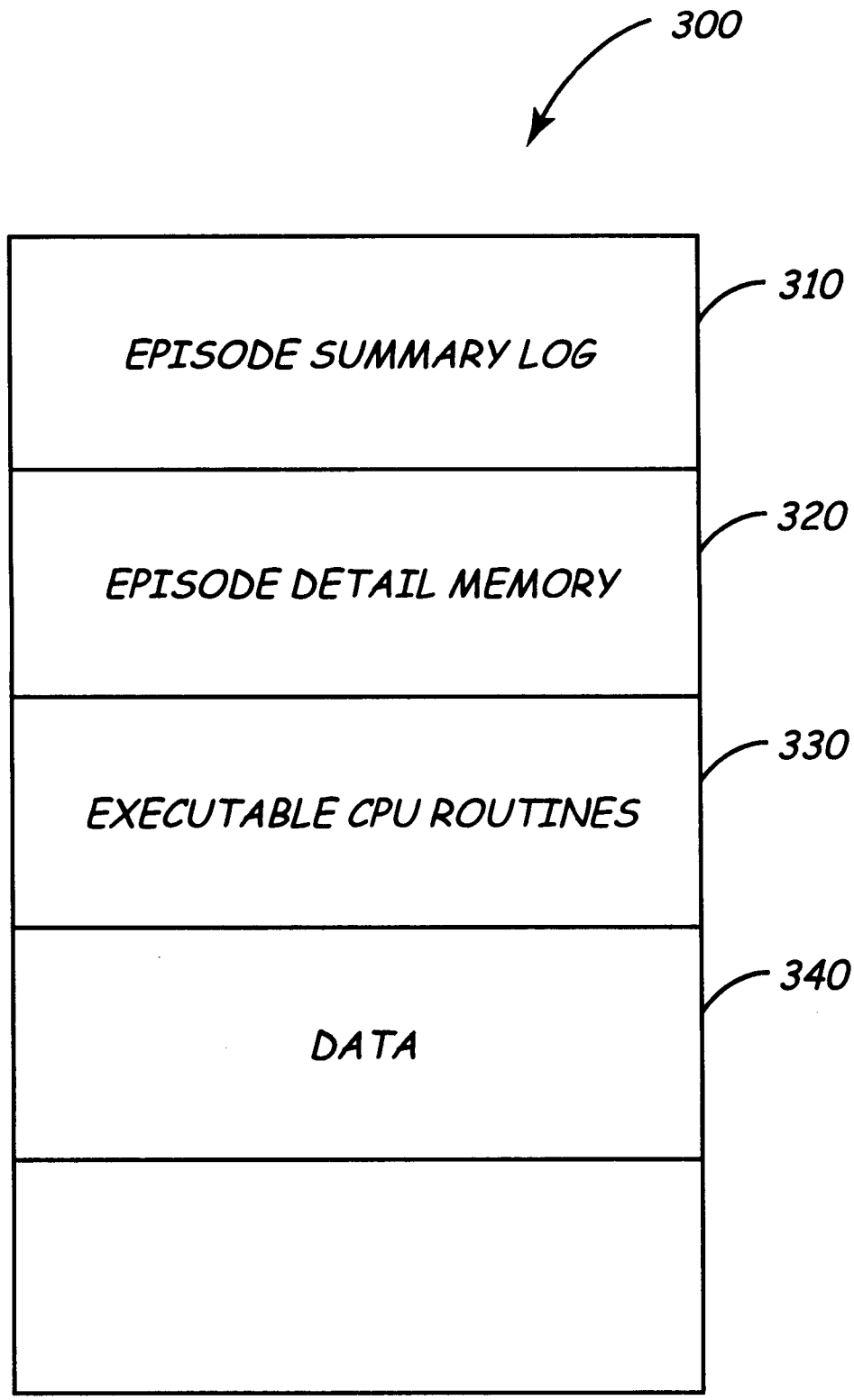
FIG. 3 is a block diagram of an illustrative random access memory in the pacemaker of FIG. 2, which memory may be used in connection with the present invention.

FIG. 3 is a simplified block diagram of one illustrative random access memory (RAM) that is suitable for use with the present invention. The RAM 300 may be used by the CPU 232 to store various executable routines and data. For example, an executable CPU routine 330 may be stored in the RAM 300 for execution by the CPU 232, and data 340 may also be stored in the RAM 300 so as to be readily accessible by the CPU 232 in connection with its execution of the executable CPU routine 330. In connection with the present invention, the CPU 232 may utilize the RAM 300 to store an episode summary log 310 and episode memory detail 320. In one particular implementation of the present invention, which will be described in greater detail below, the episode summary log 310 will include sufficient memory to store approximately 100 entries. Each entry will represent one episode of a cardiac event of interest. In this particular implementation of the present invention, the episode detail memory 320 will include sufficient memory space to store detailed EGM data and marker data associated with up to 16 separate episodes of cardiac events of interest. As will be described in further detail below, this EGM and marker data may be retrieved using the programmer 120 illustrated in FIG. 1 to enable the doctor or clinician to view the EGM data and thereby gain a more detailed understanding of any cardiac event episodes experienced by the patient. Each set of EGM and marker data stored in the episode detail memory 320 will correlate to an entry in the episode summary log 310. Thus, up to 16 of the approximately 100 episodes having an entry in the episode summary log 310 will have their associated EGM and marker data stored in the episode detail memory 320 in the RAM 300. Each entry in the episode summary log 310 will include a pointer that may be set to correlate that entry to, potentially, any of the sets of data in the episode detail memory 320, as will be explained in greater detail below.

Figure 4:
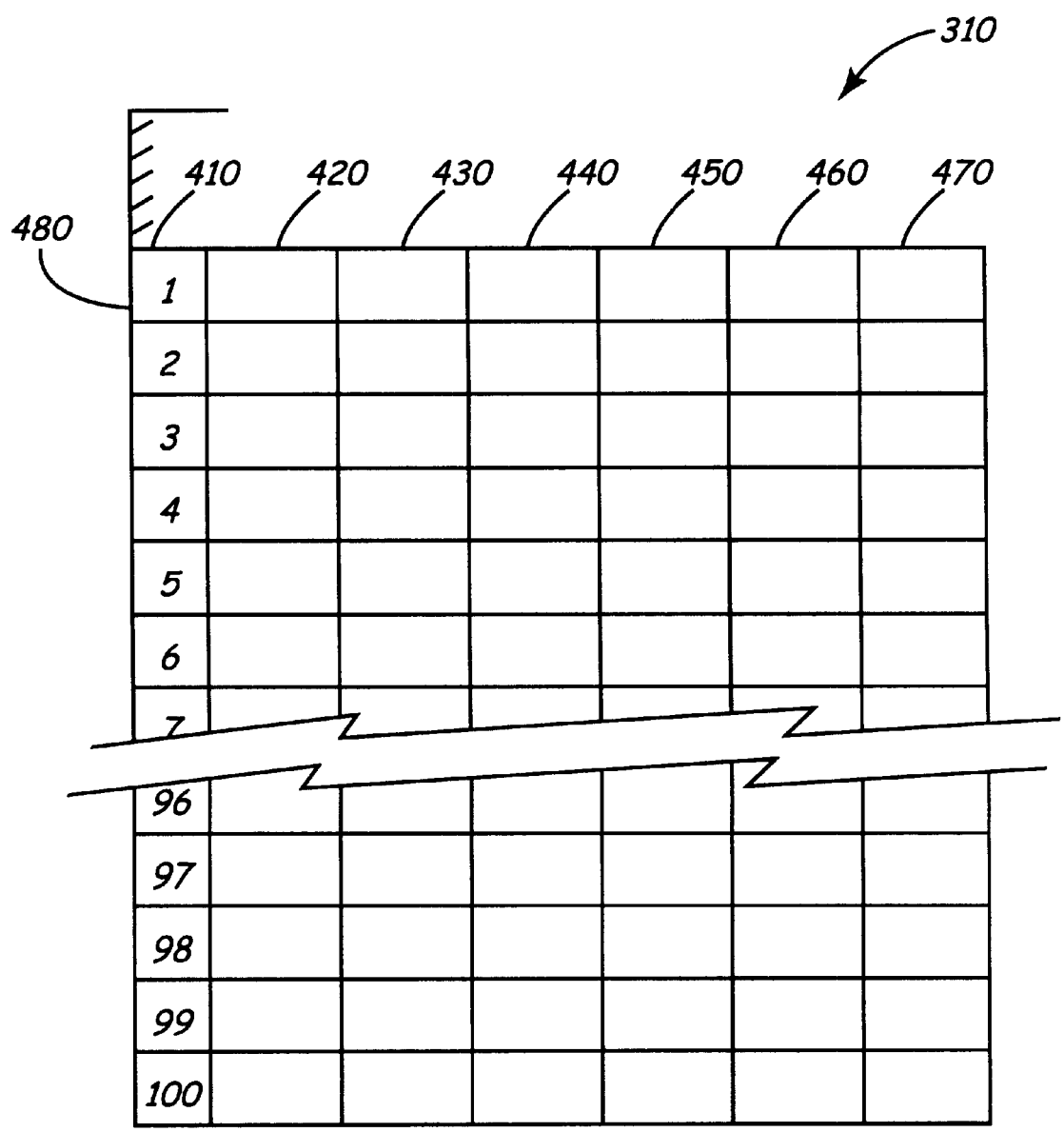
FIG. 4 illustrates one particular summary log in which a plurality of entries may be stored.

FIG. 4 illustrates the episode summary log 310 of FIG. 3 in greater detail. The episode summary log 310, in the illustrative embodiment, includes sufficient memory space for approximately 100 entries. Entries may be numbered from 1 through 100, as indicated in the column labeled 410, and each includes certain information that summarizes a particular cardiac event episode of interest. Each entry includes an indication of the cardiac event type, as indicated at 420. For example, five different cardiac event types may be of interest—ventricular tachycardia (VT), atrial tachycardia (AT), atrial fibrillation (AF), atrial flutter (Afl) and "one-to-one" (1:1). Each entry in the episode summary log 310 also includes the date 430 of the particular episode, the time 440 of that episode, the duration 450 of the episode, and the heart rate 460 observed during the episode. Each entry in the episode summary log 310 also includes a pointer 470 that may be valid or invalid, as will be explained more fully below. As explained earlier, the pacemaker 110 includes certain programming routines that are capable of detecting the onset of the various cardiac event types and initiating the collection and recordation of certain information associated with the episode, including date, time, duration and rate observed. These routines are well known to those of ordinary skill in the art.

Because the episode summary log 310 resides in the RAM 300, its contents may be altered under control of the CPU 232 or the external programmer unit 120. Upon initialization of the RAM 300, the episode summary log 310 will typically contain no entries. When a first cardiac event of interest is detected, the appropriate programming routines will detect the onset of the event and will classify the episode by event type, i.e., VT, AT, AF, Afl, or 1:1. Those routines will also record the date and time of the episode as well as the duration of the episode and the maximum heart rate observed during the episode. This information may be recorded as the first entry in the episode summary log 310. In addition, when the onset of the episode is initially detected, the appropriate programming routines will initiate the collection and recordation of the EGM data associated with the episode. As will be more fully explained below, this EGM data may be recorded into the episode detail memory 320 of the RAM 300. The location of this EGM data in the episode detail memory 320 may be recorded as the pointer 470 for the corresponding entry in the episode summary log 310. Thus, a summary entry 480 in the episode summary log 310 may include a valid pointer 470 that correlates that particular entry 480 to detailed EGM data stored in the episode detail memory 320, if such detailed EGM data exists for that summary entry 480. As will become clear, not every entry 480 in the episode summary log 310 will include detailed EGM data in the episode detail memory 320, and, thus, not every entry 480 in the episode summary log 310 will include a valid pointer 470. In particular, in the illustrative embodiment, a maximum of 16 entries in the episode summary log 310 will include detailed EGM data in the episode detail memory 320. In the particular embodiment described herein, only 15 entries from the episode summary log 310 will include a valid pointer 470.

Figure 5:
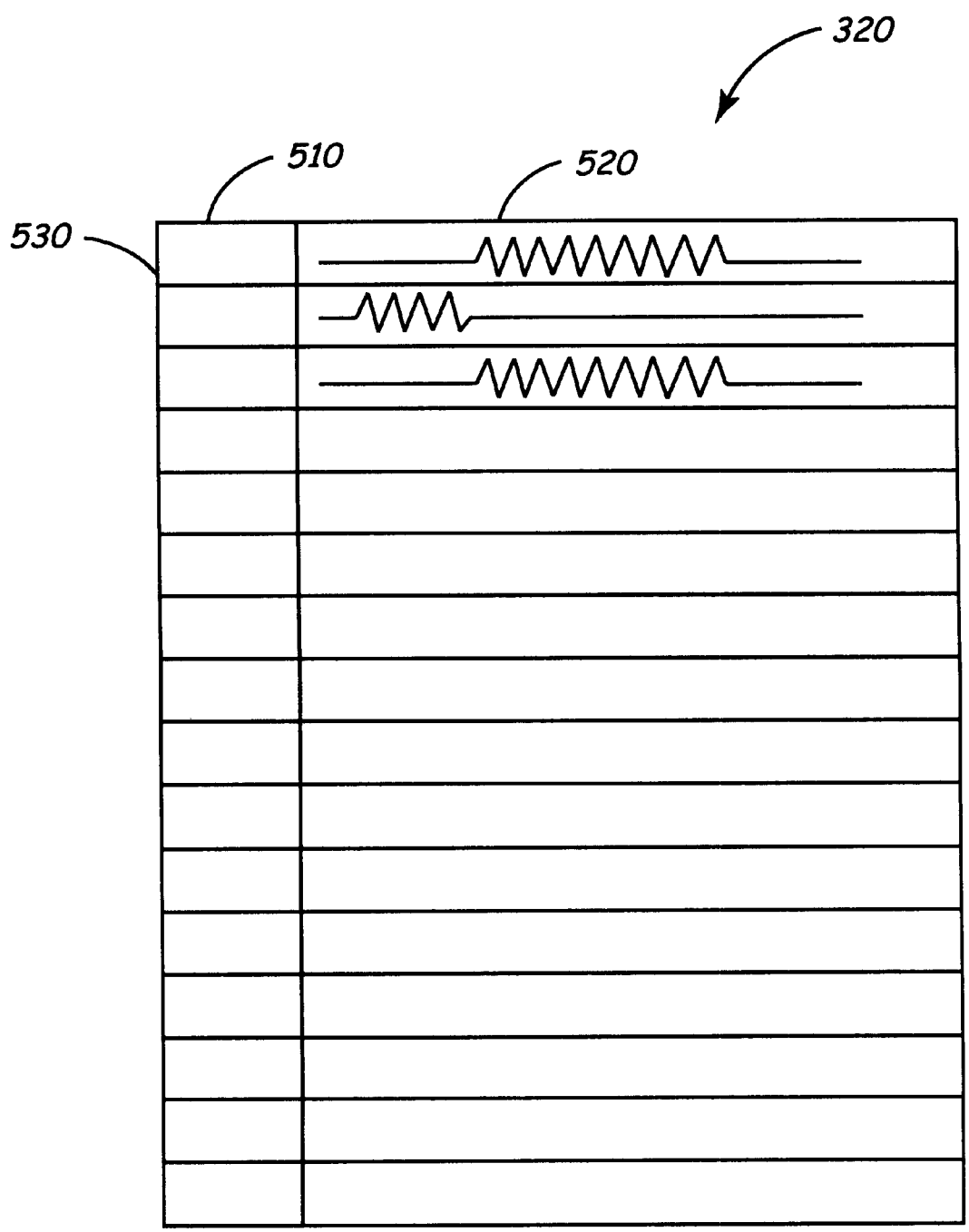
FIG. 5 illustrates one section of an illustrative detail memory in which EGM data and marker data may be stored.

FIG. 5 illustrates the episode detail memory 320 in which the EGM data and marker data are stored. The episode detail memory 320 includes sufficient RAM space to store detailed EGM and marker data associated with 16 episodes of cardiac events of interest. As already explained, after this EGM and marker data 520 is recorded in the episode detail memory 320, it may be retrieved using a variety of well known programming units in order for a doctor or clinician to view the EGM data and thereby gain a better understanding of the episodes experienced by the patient. Each set of EGM and marker data 520 included in the episode detail memory 320 has an address 510 associated with it. This address 510 may be used as the pointer 470 in the episode summary log 310 of FIG. 4.

Upon initialization of the pacemaker 110, the episode detail memory 320 will include no EGM and marker data 520. When a first episode of interest is detected, appropriate programming routines begin recording the EGM data 520 into the first available buffer 530 in the episode detail memory 320. The EGM data 520 is detected by way of the leads 114 coupled to the sense amplifier circuitry 224 in the pacemaker 110. The address 510 at which the EGM and marker data 520 are recorded may be stored as the pointer 470 in the entry 480 in the episode summary log 310 that corresponds to the episode of interest. Thus, for the first episode of interest, the episode summary log 310 will include an entry that contains information concerning the type of event, the date and time of the event, the duration of the event, the heart rate observed, and a pointer to the buffer 530 in the episode detail memory 320 that contains the corresponding EGM and marker data 520. As additional episodes are detected, additional entries may be made in the episode summary log 310 and in the episode detail memory 320. Episodes may be collected and recorded in the order in which they are received until the episode detail memory 320 is filled. As will be explained further below, after the episode detail memory 320 is filled, a priority system may be used to determine which episodes to maintain in the episode detail memory 320 and which to overwrite with new data. As will also be explained, each episode type is guaranteed storage for at least three episodes—the fastest, the longest, and the most recent. The doctor or clinician may set the priorities that will control which episode is overwritten when a new episode occurs.

Of the sixteen buffers 530 in the illustrative episode detail memory 320, a maximum of fifteen of the buffers 530 may contain valid EGM and marker data 520 at any given time. The sixteenth buffer 530 is designated as the "scratch buffer." The scratch buffer is that location into which the EGM and marker data 520 for the next-occurring episode will be recorded. Thus, for example, after fifteen episodes have been recorded into the episode detail memory 320, the onset of a sixteenth episode will result in the EGM data 520 for that episode to be recorded into the sixteenth buffer 530, designated the scratch buffer. When the episode is terminated and the episode has been classified by event type, a determination may be made as to which set of EGM data 520 of the previous fifteen episodes will be "thrown out," as will be explained below.

Referring now to FIG. 6, in the illustrative embodiment, a set of pointers may be used to identify locations in the episode detail memory 320 that contain EGM and marker data 520 for significant episodes. FIG. 6 illustrates one particular pointer set 600 that may be used in the illustrative embodiment. The pointer set 600 of FIG. 6 is implemented in the form of a set of sixteen registers 610A–610Q. The sixteen registers 610A–610Q may store sixteen pointers to the episode detail memory 320. As one example of the use of the pointer set 600, a doctor or clinician may desire to collect EGM data associated with five cardiac event types— VT, AT, AF, Afl and "one-to-ones." For each event type, the doctor or clinician may desire to collect EGM data for the longest-lasting episode, for the episode in which the fastest heart rate is observed, and for the last-occurring episode.

The registers 610A–610Q of the illustrative pointer set 600 may be designated as follows: the registers 610A–610C may store pointers (to the episode detail memory 320) for the EGM data for the "longest VT," the "fastest VT," and the "last VT," respectively; the registers 610D–610F may store pointers for the EGM data for the "longest AT," the "fastest AT," and the "last AT," respectively; the registers 610G–610I may store pointers for the EGM data for the "longest AF," the "fastest AF," and the "last AF," respectively; the registers 610J–610L may store pointers for the EGM data for the "longest Afl," the "fastest Afl," and the "last Afl," respectively; and the registers 610M–610P may store pointers for the EGM data for the "longest 1:1," the "fastest 1:1," and the "last 1:1," respectively. The register 610Q may store a pointer for the scratch buffer in the episode detail memory 320.

As discussed above, upon initialization of the RAM 300, the episode detail memory 320 will contain no EGM or marker data and the episode summary log 310 will contain no entries. The first fifteen episodes experienced by the patient, regardless of event type, will cause entries to be made in the episode summary log 310, and EGM and marker data for those fifteen episodes will be stored in the episode detail memory 320. Moreover, each of the fifteen entries in the episode summary log 310 will include a valid pointer 470 identifying the location in the episode detail memory 320 where the corresponding EGM and marker data is stored. The fifteen recorded episodes may be all of the same event type (e.g., VT), or they may be any combination of the five event types (i.e., VT, AT, AF, Afl, 1:1).

In addition, the pointer set 600 may also contain one or more entries. For example, if a VT event has occurred in the first fifteen episodes, the "last VT" point (e.g., register 610C) will identify the location in the episode detail memory 320 storing the EGM and marker data for the last-occurring VT event. Likewise, the "longest VT" and "fastest VT" pointers will identify the appropriate locations in the episode detail memory 320 (although if, for example, only a single VT event has occurred, all three VT pointers 610A–610C may indicate the same location in the episode detail memory). As a further example, if more than three VT events have occurred in the initial fifteen episodes, and if the VT events all had different durations and different maximum heart rates, the three VT registers 610A, 610B, 610C may each contain a different pointer to the episode detail memory 320. No more than three VT pointers will be stored in the particular pointer set 600 illustrated n FIG. 6 as its allocation is indicated.

After fifteen episodes have been detected and recorded in the episode detail memory 320, when a sixteenth episode is detected, the EGM and marker data for this sixteenth episode will be recorded at the location in the episode detail memory 320 identified by the scratch buffer pointer 610Q in the pointer set 600. Also, an entry is made in the episode summary log 310 for the sixteenth episode. When the sixteenth episode has terminated and the episode has been classified by event type, the following steps are performed in the illustrative embodiment:

(1) The "last" pointer in the pointer set 600 for the episode type is set to the scratch location, the sixteenth buffer 530. By definition, this most recent (sixteenth) episode is the "last" episode for that event type.

(2) The episode is examined to determine if it is the longest in duration for its event type or the fastest rate observed for its event type. If this episode is determined to be the longest in duration for its event type, the "longest" episode pointer for that event type is set to the scratch location, the sixteenth buffer 530. If the episode is determined to contain the fastest rate observed for its event type, the "fastest" episode pointer for that event is set to the scratch location.

(3) An episode count for each cardiac event type is maintained in an accumulation register, and the count for the event type represented by the most recent episode is incremented.

Upon receipt of the sixteenth episode, the following rules will be used to determine which episode to discard and assign to the new scratch buffer location:

(1) Each event type is guaranteed storage for at least three episodes.

(2) Episode storage will be prioritized by type.

(3) The new scratch buffer location will be the oldest episode (that is not the fastest or longest) of the lowest priority type that has more than three episodes recorded. This location will become the new pointer in the register 610Q in the pointer set 600.

In the illustrative embodiment, the five cardiac event types of interest are prioritized as follows: VT events are of the highest priority, priority one; one-to-ones are of the second highest priority, priority two; AF events are the next highest priority, priority three; Afl events are the next highest priority, priority four; and AT events are the lowest priority, priority five. If all episode types have occurred, each type will have storage for at least three episodes—the fastest, the longest, and the most recent.

However, not all event types may occur, and/or fewer than three episodes of a particular event type may occur, while many more than three episodes of yet another event type may occur. In that situation, the episode detail memory 320 may store EGM and marker data for more than three episodes of a given event type. This dynamic allocation of memory space in the episode detail memory 320 ensures that available memory space in the episode detail memory 320 will not go unused while valuable episode data is needlessly discarded. Fifteen episode details will always be available (as long as at least fifteen episodes occur), so the episode detail memory 320 will accumulate data based on what event types are actually occurring. And after the episode detail memory 320 is filled, subsequent episodes will cause only the lowest priority and least important data then existing in the episode detail memory 320 to be discarded.

FIG. 7 depicts a portion 700 of a method implementing aspects of the present invention. The portion 700 of the illustrative method begins, at 710, as a fifteenth episode is recorded in the episode summary log 310 and in the episode detail memory 320. Following recordation of this fifteenth episode, the pointers in the pointer set 600 are updated, as noted at 720, at which time at least some of the registers 610A–610P in the pointer set 600 will have valid pointers, depending upon the cardiac event type observed, for example. Also, the register 610Q in the pointer set 600 will contain the location of the scratch buffer (the sixteenth buffer) in the episode detail memory 320.

As noted at 730, when the next episode is detected, the EGM and marker data for that episode will be recorded in the scratch buffer location of the episode detail memory 320, that location being identified by the pointer in the register 610Q in the pointer set 600. In addition, a summary entry concerning the episode will be recorded in the episode summary log 310, and, because the EGM data will be preserved as the "last" episode of the particular event type, the pointer field 470 in the summary entry for this episode will be set to the location of the scratch buffer. As noted at 740, the pointers in the pointer set 600 will again be updated as follows:

(1) the "last" pointer for the appropriate event type will be set to the location of the scratch buffer;

(2) the CPU, using an appropriate routine, will determine if this latest episode is the "longest" of its type, and, if it is, the "longest" pointer for that event type will be set to the location of the scratch buffer; otherwise, the "longest" pointer will remain unchanged; and (3) the CPU will determine if this latest episode included the "fastest" heart rate of the other recorded episodes of this event type, and, if it does, the "fastest" pointer for this event type will be set to the location of the scratch buffer; otherwise, the "fastest" pointer will remain unchanged.

Because the original scratch buffer now contains valid data to be retained, the CPU must determine which of the other fifteen sets of EGM data in the episode detail memory may be overwritten by the next incoming episode, as seen at 750. To make this selection, the CPU determines which of the fifteen sets of EGM data relates to the oldest episode (but not including a "longest" or "fastest" episode of any event type) of the lowest priority event type which has more than three episodes recorded. Alternatively, all sixteen sets of EGM data may be evaluated when determining the new scratch buffer. The location of the set of EGM data meeting these criteria will then be designated as the new scratch buffer in the episode detail memory 320. This location will be identified by updating the pointer in register 610Q in the pointer set 600. Finally, as noted at 760, the summary entry 480 in the episode summary log 310 that contains, as its pointer 470, the location of the new scratch buffer in the episode detail memory 320 will have its pointer invalidated because that EGM data is no longer available and will be overwritten by the next episode.

Table 1 below gives examples of the episode dynamic memory allocation that may occur in the illustrative embodiment under exemplary circumstances.

TABLE 1

Episode Dynamic Memory Allocation Examples

| State Before | What Occurred | State After |
|---|---|---|
| 5 VTs<br>2 1:1s<br>3 AFs<br>1 Afl<br>4 ATs | Afl episode is received. Afl is saved. Afl count is incremented to 2. Because AT is the lowest priority type and more than 3 ATs are stored, the oldest AT (that is not fastest or longest) becomes the scratch buffer. AT count is decremented to 3. | 5 VTs<br>2 1:1s<br>3 AFs<br>2 Afls<br>3 ATs |
| 5 VTs<br>2 1:1s<br>3 AFs<br>2 Afls<br>3 ATs | AT episode is received. AT is saved. AT count is incremented to 4. Because AT is the lowest priority type and more than 3 ATs are stored, the oldest AT (that is not fastest or longest) becomes the scratch buffer. AT count is decremented to 3. | Same as before except that a different AT is stored. |
| 15 Afls | VT episode is received. VT is saved. VT count is incremented to 1. Because VTs are guaranteed at least 3 storage locations, the oldest Afl (that is not fastest or longest) becomes the scratch buffer. Afl count is decremented to 14. | 1 VT<br>14 Afls |
| 4 VTs<br>11 Afls | Afl episode is received. Afl is saved. Afl count is incremented to 12. Because Afl is lowest priority type with more than 3, the oldest Afl (that is fastest or longest) becomes the scratch buffer. Afl count is decremented to 11. | Same state as before except that a different Afl is stored. |
| 13 VTs<br>2 Afls | AT episode is received. AT is saved. AT count is incremented to 1. Afls are the lowest priority type but they do not have more than 3 so a VT must be given up. So the oldest VT (that is not fastest or longest) becomes the scratch buffer. VT count is decremented to 12. | 12 VTs<br>2 Afls<br>1 AT |

Using the apparatus and method of the present invention, a doctor or clinician may retrieve summary information related to a relatively large number of cardiac event episodes of interest. He or she may also retrieve detailed EGM and marker data associated with at least some of the episodes observed. Moreover, the doctor or clinician need not decide in advance what particular cardiac event types may be of interest so as to more efficiently utilize available memory space. Rather, the available memory space will be fully utilized and will be allocated dynamically based upon the types of events observed and the priorities set for recording those events.

The particular embodiments disclosed above are illustrative only, as the invention may be modified and practiced in different but equivalent manners apparent to those skilled in the art having the benefit of the teachings herein. For example, the process steps set forth above may be performed in a different order. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed is:

1. A software system implemented in a medical device for allocating storage for cardiac data using a method of an allocation scheme, the method comprising:

storing said cardiac data in a plurality of addressable locations, said cardiac data being associated with various types of cardiac episodes;

determining whether all available locations within said plurality of addressable locations are full; and assigning a scratch location within said plurality of addressable locations based on predetermined episode type priorities and characteristics.

2. The method of claim 1, wherein said priorities include a graduated order based on the clinical significance of said cardiac episodes.

3. The method of claim 1 wherein said characteristics include classifications based on fastest rate, longest duration and last to occur for each of said priorities.

4. The method of claim 3 wherein said cardiac episode represented by said characteristics for each of said priorities is immunized from scratch and ensured allocation space.

5. The method of claim 4 wherein the allocation scheme includes a process of assigning storage for each of said priorities that is immunized while ensuring the availability of at least one location for sharing data for the next cardiac episode.

6. An apparatus in an implantable cardiac device, comprising:

an episode summary log memory adapted to store a plurality of entries, each entry correlating to a cardiac event episode; and an episode detail memory adapted to store a plurality of cardiac data, each set of cardiac data correlating to a particular cardiac event episode, wherein at least one an episode detail memory adapted to store a plurality of cardiac data, each set of cardiac data correlating to a particular cardiac event episode, wherein at least one entry in the episode summary log memory is adapted to include a pointer to a corresponding at least one set of cardiac data in the episode detail memory.

7. The apparatus of claim 6, wherein each of the plurality of entries in the episode summary log memory includes a date and time when a cardiac event episode occurred, a duration of the cardiac event episode, and a maximum heart rate detected during the cardiac event episode.

8. The apparatus of claim 6, wherein each of the plurality of sets of cardiac data includes cardiac data and marker data.

9. The apparatus of claim 6, wherein the episode summary log memory is at least a portion of a random access memory.

10. The apparatus of claim 6, wherein the episode detail memory is at least a portion of a random access memory.

11. The apparatus of claim 6, wherein the episode summary log memory is adapted to store approximately 100 entries.

12. The apparatus of claim 11, wherein the episode detail memory is adapted to store a maximum of sixteen sets of EGM data.

13. An apparatus in an implantable cardiac device, comprising:

an episode summary log memory adapted to store a plurality of entries, each entry correlating to a cardiac event episode; and an episode detail memory adapted to store a plurality of cardiac data, each set of cardiac data correlating to a particular cardiac event episode, wherein at least one entry in the episode summary log memory is adapted to include a pointer to a corresponding at least one set of cardiac data in the episode detail memory;

wherein the episode summary log memory is adapted to store approximately 100 entries;

wherein, the episode detail memory is adapted to store up to fifteen sets of EGM data; and wherein the apparatus further comprises a scratch buffer in the episode detail memory adapted to receive a set of cardiac data correlating to a most-recently-detected cardiac event episode.

14. The apparatus of claim 6, wherein the episode detail memory is adapted to store a maximum of sixteen sets of cardiac data.

15. The apparatus of claim 6, wherein the episode detail memory is adapted to store up to fifteen sets of EGM data, and wherein the apparatus further comprises a scratch buffer in the episode detail memory adapted to receive a set of EGM data correlating to a most-recently-detected cardiac event episode.

16. The apparatus of claim 13, wherein the pointer in the at least one entry in the episode summary log memory is adapted to be invalidated in response to receipt by the scratch buffer of a set of EGM data.

17. The apparatus of claim 6, further comprising a plurality of significant event pointers, each significant event pointer adapted to identify a set of EGM data in the episode detail memory.

18. The apparatus of claim 17, further comprising a scratch buffer pointer adapted to identify a location in the episode detail memory where a set of EGM data associated with a next-occurring cardiac event episode may be recorded.

* * * * *